(12) United States Patent
Komatsu et al.

(10) Patent No.: US 11,244,552 B2
(45) Date of Patent: Feb. 8, 2022

(54) WATCHING SYSTEM, WATCHING METHOD, AND RECORDING MEDIUM

(71) Applicant: HITACHI, LTD., Tokyo (JP)

(72) Inventors: Yuto Komatsu, Tokyo (JP); Hirokazu Atsumori, Tokyo (JP); Tsukasa Funane, Tokyo (JP); Akiko Obata, Tokyo (JP); Akihiko Kandori, Tokyo (JP)

(73) Assignee: HITACHI, LTD, Tokyo (JP)

( * ) Notice: Subject to any disclaimer, the term of this patent is extended or adjusted under 35 U.S.C. 154(b) by 0 days.

(21) Appl. No.: 16/988,099

(22) Filed: Aug. 7, 2020

(65) Prior Publication Data

US 2021/0082270 A1 Mar. 18, 2021

(30) Foreign Application Priority Data

Sep. 13, 2019 (JP) .............................. JP2019-167025

(51) Int. Cl.
  *G08B 21/04* (2006.01)
  *A61B 5/11* (2006.01)
(52) U.S. Cl.
  CPC .......... *G08B 21/043* (2013.01); *A61B 5/1114* (2013.01); *A61B 5/1115* (2013.01); *A61B 5/1117* (2013.01); *A61B 5/1128* (2013.01); *G08B 21/0476* (2013.01)
(58) Field of Classification Search
  CPC .. G08B 21/043; G08B 21/04; G08B 21/0476; A61B 5/1117; A61B 5/11; A61B 5/1114; A61B 5/1128; A61B 5/1127; A61B 5/1115
  See application file for complete search history.

(56) References Cited

U.S. PATENT DOCUMENTS 5,979,586 A * 11/1999 Farmer ................. B60Q 9/008
                                                                                180/274
2012/0075464 A1* 3/2012 Derenne ................ A61B 5/112
                                                                                348/135

FOREIGN PATENT DOCUMENTS

JP        2015-164477 A        9/2015
JP        2017-176244 A        10/2017

* cited by examiner

*Primary Examiner* — Nabil H Syed
*Assistant Examiner* — Cal J Eustaquio
(74) *Attorney, Agent, or Firm* — Volpe Koenig (57) ABSTRACT

A watching system, which calculates a fall probability of an imaged person to be fallen using a computer which includes a processor and a memory, includes a trunk extraction unit that receives time-series skeleton information of the imaged person, calculates an angle between a head and a waist of the imaged person based on the skeleton information, extracts the angle as a trunk of the imaged person, calculates the center of the trunk as a trunk center based on trunk information set in advance, extracts a trunk to be reference as a reference trunk from a time-series trunk calculated from the time-series skeleton information, and holds a center of the reference trunk, and a fall probability calculation unit that calculates a distance between a trunk center of the reference trunk and a trunk center of the trunk as a deviation amount, and calculates the fall probability from the deviation amount.

15 Claims, 8 Drawing Sheets

WATCHING SYSTEM, WATCHING METHOD, AND RECORDING MEDIUM

CLAIM OF PRIORITY

The present application claims priority from Japanese patent application JP2019-167025 filed on Sep. 13, 2019, the content of which is hereby incorporated by reference into this application.

BACKGROUND OF THE INVENTION

1. Field of the Invention

The present invention relates to a watching system and a watching method for detecting a sign of a fall of a human body.

2. Description of the Related Art

In JP 2015-164477 A and JP 2017-176244 A, there are known devices for observing a motion of a human body and detecting a specific motion. JP 2015-164477 A discloses a system that predicts a fall due to a stumbling at a step on the basis of leg data including a height of a knee joint during walking and a swing-up angular velocity of a thigh, and time-series data of step information.

JP 2017-176244 A discloses an apparatus for predicting a fall from an index for evaluating posture stability and posture information at the time of a cross test by the cross test using a body sway meter.

SUMMARY OF THE INVENTION

In the above-described conventional technology, a fall during walking is predicted by attaching a position sensor or an acceleration sensor to the subject or using a body sway meter, but a fall other than the walk cannot be detected or predicted.

For example, when there is a symptom that the posture is difficult to maintain, a fall may occur even other than during walking, and in many cases, the fall pattern is different from the normal fall pattern. Therefore, it is extremely difficult to collect the learning data. If there is a symptom that is difficult to maintain the posture, it may fall to the side from the state of sitting on the bed, but with the above-described conventional technology, it is impossible to predict a sign of a fall or a fall from the sitting posture.

The invention has been made in view of the above problems, and an object thereof is to detect a sign of a fall of a human body including a sitting posture.

According to the invention, there is provided a watching system which calculates a fall probability of an imaged person to be fallen using a computer which includes a processor and a memory. The watching system includes a trunk extraction unit that receives time-series skeleton information of the imaged person, calculates an angle between a head and a waist of the imaged person based on the skeleton information, extracts the angle as a trunk of the imaged person, calculates a center of the trunk as a trunk center based on trunk information set in advance, extracts a trunk to be reference as a reference trunk from a time-series trunk calculated from the time-series skeleton information, and holds a center of the reference trunk, and a fall probability calculation unit that calculates a distance between a trunk center of the reference trunk and a trunk center of the trunk as a deviation amount, and calculates the fall probability from the deviation amount.

Therefore, according to the invention, it is possible to detect a sign of a fall with high accuracy, including a sitting posture, based on a change in the trunk of a human body.

The details of at least one implementation of the subject matter disclosed herein are set forth in the accompanying drawings and the description below. Other features, aspects, and advantages of the disclosed subject matter will be apparent from the following disclosure, drawings, and claims.

DESCRIPTION OF THE PREFERRED EMBODIMENTS

Hereinafter, embodiments of the invention will be described on the basis of the accompanying drawings.

First Embodiment

Figure 1:
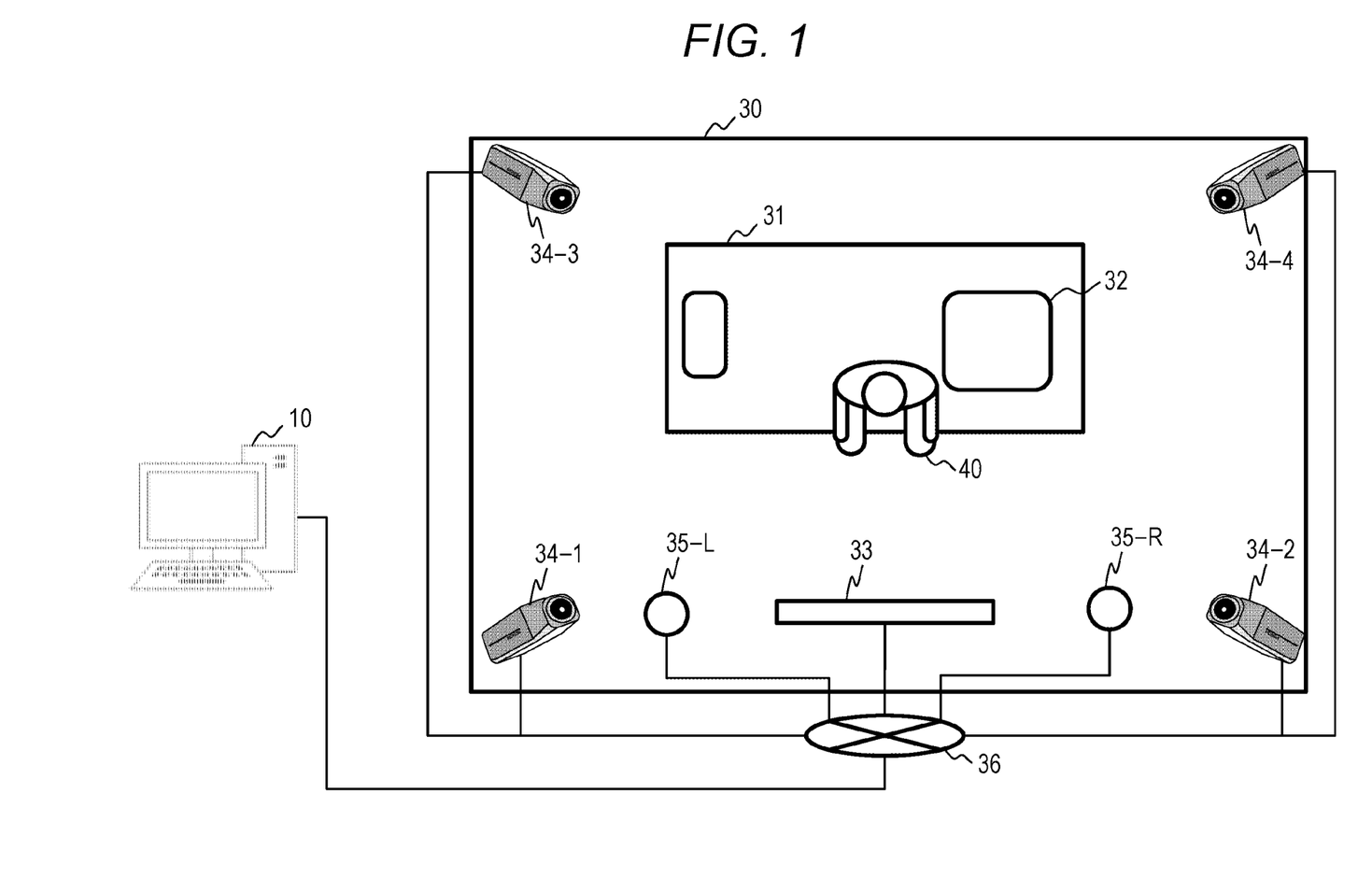
FIG. 1 is a diagram illustrating an example of a configuration of a watching system of a first embodiment of the invention.

FIG. 1 is a diagram illustrating a first embodiment of the invention, and illustrating an example of a configuration of a watching system. In this embodiment, an example of a watching system for watching a person having a symptom or a dysfunction in which it is difficult to maintain a posture will be described.

An illustrated living room 30 is a plan view. A bed 31 used by a subject 40 is installed in a living room 30, and cameras 34-1 to 34-4 for capturing the subject 40 are installed in the four corners of the living room 30. A monitor 33 is provided between the cameras 34-1 and 34-2 facing the long side of the bed 31. In the following description, in a case where the cameras are not individually specified, the reference numeral "34" in which the part after "-" is omitted is used. The same applies to reference numerals of other components.

A light 35-L is provided between the monitor 33 and the camera 34-1, and a light 35-R is provided between the monitor 33 and the camera 34-2. The monitor 33, the cameras 34, and the lights 35 are connected to the computer 10 via a network 36.

The computer 10 acquires a moving image of the camera 34, detects the state of the subject 40, and displays a predetermined image on the monitor 33 when detecting a sign of the fall of the subject 40, and turns on the light 35 as described below. Further, a cushion 32 arranged on the bed 31 buffers an impact when the subject 40 falls.

Further, the subject 40 in the drawing illustrates a state in which the subject 40 is sitting on the bed 31 facing the monitor 33. Further, in this embodiment, an example in which the subject 40 is captured by four cameras 34 is illustrated. However, the number may be any number that can detect a sign of a fall, and it is also possible to capture with one camera 34.

Figure 2:
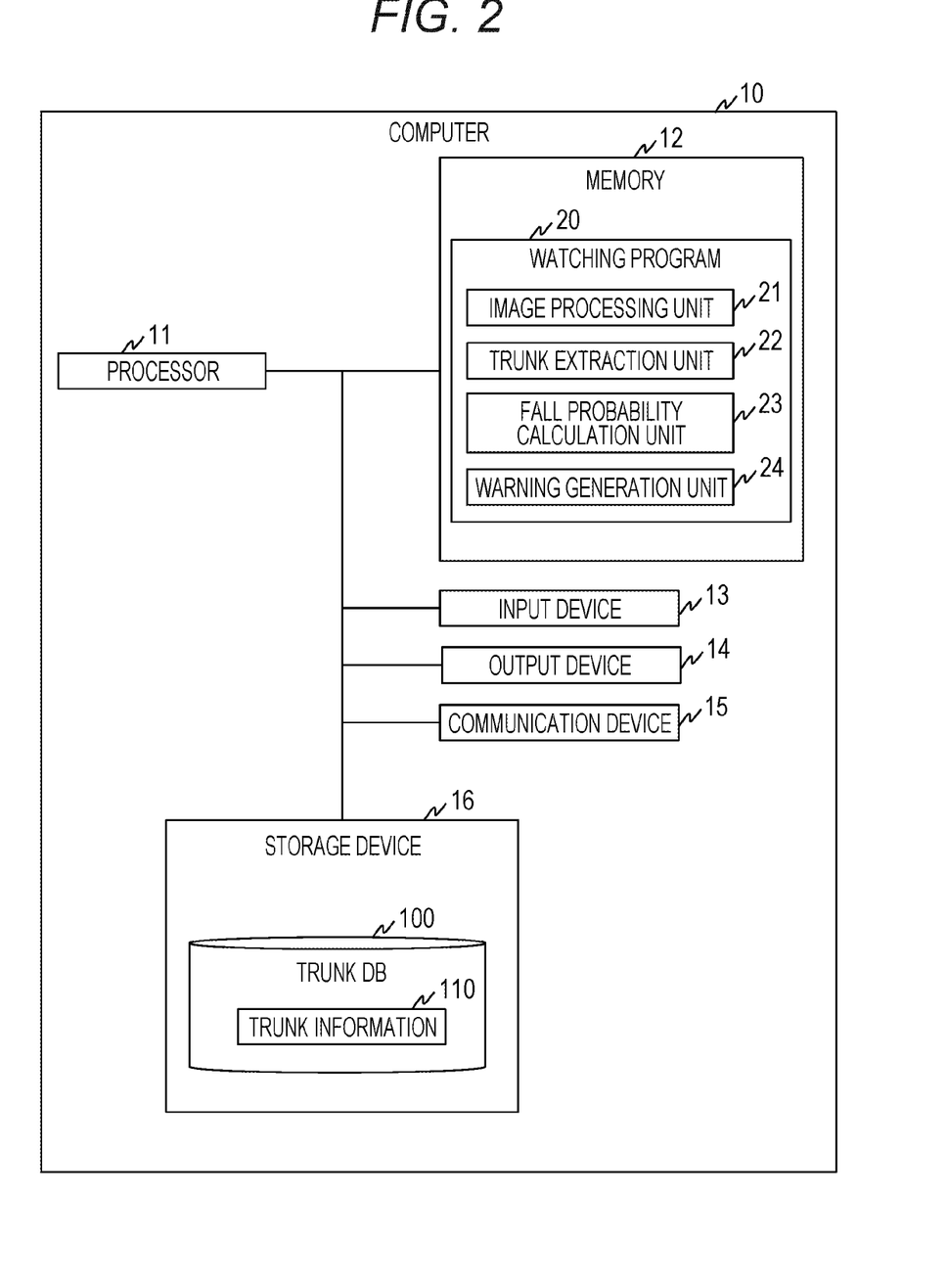
FIG. 2 is a block diagram illustrating an example of a configuration of a computer according to the first embodiment of the invention.

FIG. 2 is a block diagram illustrating an example of the configuration of the computer 10. The computer 10 includes a processor 11, a memory 12, an input device 13, an output device 14, a communication device 15, and a storage device 16.

A watching program 20 is loaded into the memory 12 and executed by the processor 11. The watching program 20 includes an image processing unit 21, a trunk extraction unit 22, a fall probability calculation unit 23, and a warning generation unit 24.

The image processing unit 21 acquires moving images from the four cameras 34, respectively, aligns the time series of images (frames), and outputs the images to the trunk extraction unit 22. The trunk extraction unit 22 calculates the trunk and trunk center of the subject 40 from the image of the camera 34 as described later, and calculates a deviation amount D of the trunk center, an acceleration α of the trunk center, and an angle β of the trunk as described later.

The fall probability calculation unit 23 calculates a fall probability P of the subject 40 from the deviation amount D of the trunk center, the acceleration α, and the angle β of the trunk calculated by the trunk extraction unit 22 as described later.

Each functional unit of the image processing unit 21, the trunk extraction unit 22, the fall probability calculation unit 23, and the warning generation unit 24 is loaded into the memory 12 as a program.

The processor 11 operates as a functional unit which provides a predetermined function by performing processing according to the program of each functional unit. For example, the processor 11 functions as the image processing unit 21 by performing processing according to an image processing program. The other programs are performed similarly. Further, the processor 11 operates also as a functional unit which provides each function of the plurality of processing performed by the programs. A computer and a computer system are devices or systems which include these functional units.

The input device 13 includes a keyboard, a mouse, a touch panel, and the like. The output device 14 includes, for example, a display. The communication device 15 is connected to the network 36 and communicates with devices in the living room 30.

The storage device 16 stores a trunk database 100 that manages trunk information 110 of the subject 40. The trunk information 110 holds position information of the trunk center preset for each subject 40 and an identifier of the subject 40.

Figure 3:
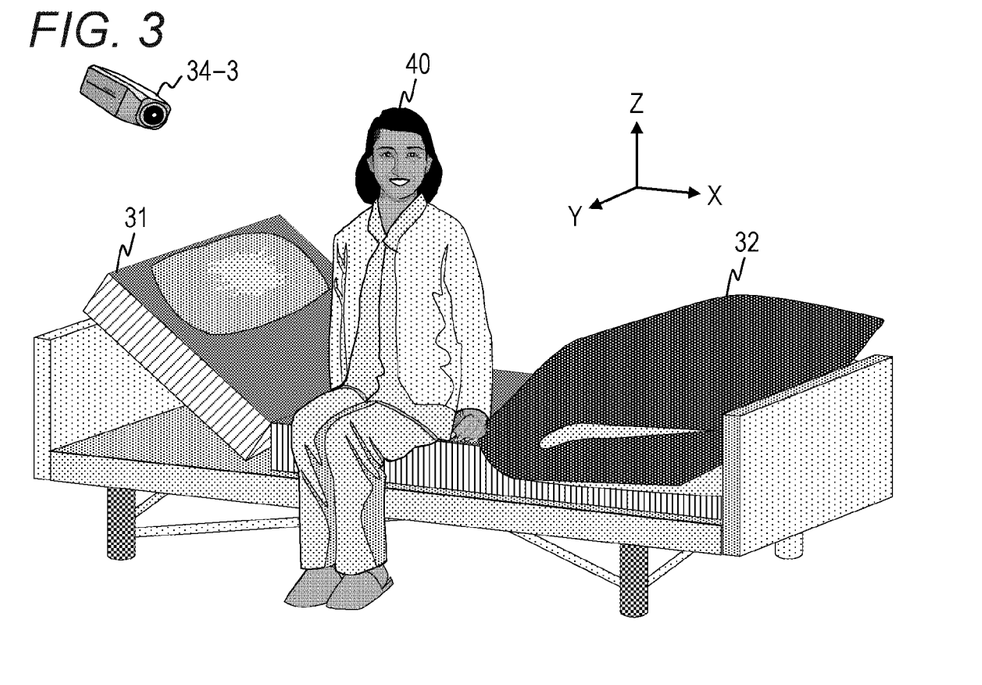
FIG. 3 is a perspective view illustrating an example of a space in a living room of the first embodiment of the invention.

FIG. 3 is a perspective view illustrating an example of the subject 40 in the living room 30. The bed 31 can adopt a gatch-up bed or the like that can adjust the height of the back and the legs.

The cameras 34 are installed from predetermined heights at four corners in the living room 30 toward the center of the bed 31, and capture images of the subject 40 at a predetermined frame rate (for example, 30 fps). In order to calculate a falling direction of the subject 40, the longitudinal direction of the bed 31 is set as an X axis, the width direction of the bed 31 is set as a Y axis, and the vertical direction of the living room 30 is set as a Z axis.

Figure 4:
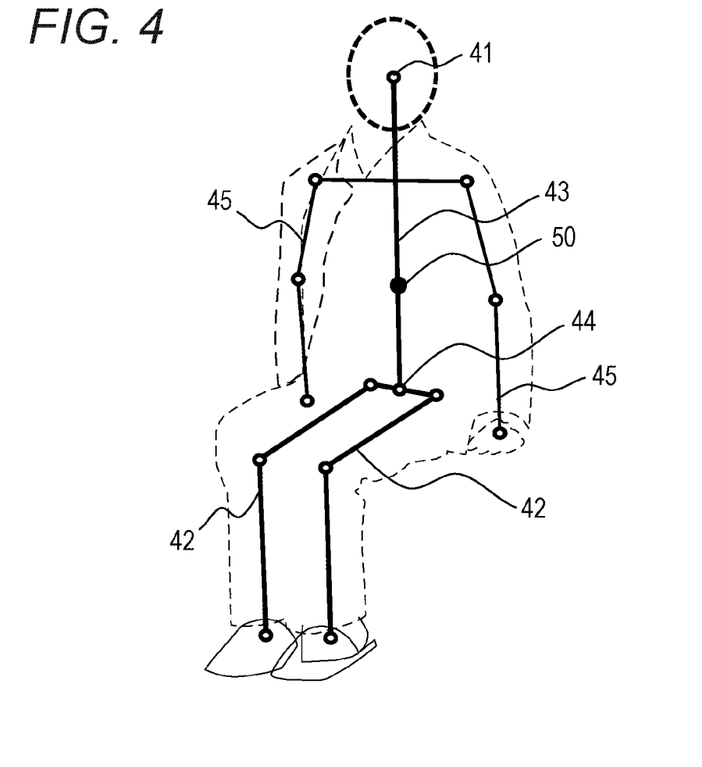
FIG. 4 is a diagram illustrating an example of a trunk in a sitting posture of the first embodiment of the invention.

FIG. 4 is a diagram illustrating an example of the trunk of the subject 40 in the sitting posture. The trunk extraction unit 22 calculates a trunk 43, a leg 42, an arm 45, and a trunk center 50 from the image of the camera 34. The trunk extraction unit 22 calculates a head center 41 and a waist center 44 from the image of the camera 34, and calculates the angle of the trunk 43 connecting the head center 41 and the waist center 44. Further, the angle is calculated as an angle with respect to a preset reference axis (for example, the Z axis).

As a method for calculating the head center 41, the waist center 44, the legs 42, and the arms 45 from the image of the camera 34, for example, skeletons or joints may be extracted using a known or well-known technique such as JP 2019-66238 A and JP 2019-96328 A. Hereinafter, information on a skeleton position and a joint position estimated from the image will be simply referred to as a skeleton, a joint, and the like.

The trunk extraction unit 22 sets the center of the pelvis estimated and extracted from the image of the camera 34 as the waist center 44 and the center of the head extracted from the image of the camera 34 as the head center 41. The trunk extraction unit 22 calculates the angle of a straight line connecting the legs 42 and the arms 45 to the skeletons and joints extracted from the image of the camera 34.

The trunk extraction unit 22 calculates the angle of the trunk 43, the legs 42, or the like. A front image of the subject 40 from the image of each camera 34 is synthesized, and the angle can be calculated as an angle in the front image. Alternatively, the angle of a line segment in the three-dimensional space of X, Y, and Z illustrated in FIG. 3 may be used.

The trunk extraction unit 22 acquires the position of the trunk center 50 preset for each subject 40 with reference to the trunk information 110 of the trunk database 100. The position of the trunk center 50 is set, for example, by the ratio of the distance from the waist center 44 to the head center 41.

For example, the position of 30% of the distance from the waist center 44 to the head center 41 is defined as the position of the trunk center 50. The position (ratio) of the trunk center 50 is set in advance by an expert or the like in consideration of individual differences for each subject 40 and registered in the trunk information 110 of the trunk database 100.

In this embodiment, an example in which the position (ratio) of the trunk center 50 is set for each subject 40 in order to detect a sign of a fall with high accuracy. However, when high accuracy is not required, a fixed value may be used.

The trunk extraction unit 22 holds a reference trunk 43S determined from the trunk 43 calculated in time series and the trunk center 50 of the reference trunk 43S as a reference.

Figure 5:
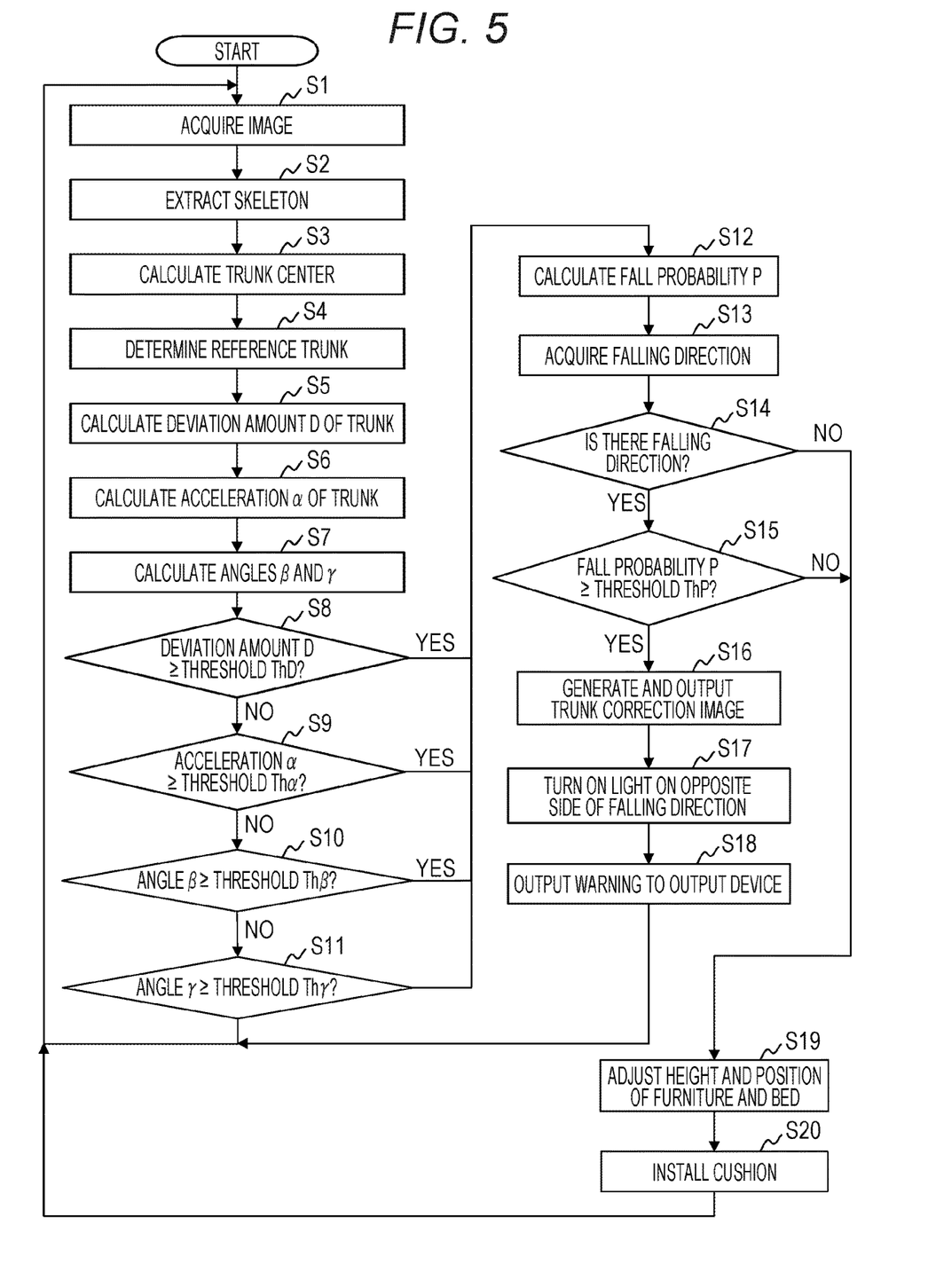
FIG. 5 is a flowchart illustrating an example of a process performed by a computer of the first embodiment of the invention.

FIG. 5 is a flowchart illustrating an example of the process performed in the computer 10. In the watching program 20 of the computer 10, first, the image processing unit 21 acquires an image of the subject 40 from the camera 34 (S1).

Next, the trunk extraction unit 22 extracts a skeleton from the image of the subject 40, and calculates the head center 41, the waist center 44, and the legs 42 as illustrated in FIG. 4 (S2). The trunk extraction unit 22 acquires the position of the trunk center of the subject 40 with reference to the trunk information 110 of the trunk database 100. The trunk extraction unit 22 calculates the angle of a straight line connecting the head center 41 and the waist center 44 as the trunk 43, and calculates the trunk center 50 from the position of the trunk center in the trunk information 110 (S3).

Next, the trunk extraction unit 22 determines the trunk as a reference. Regarding the reference trunk, for example, the trunk 43 in which an angle formed by the Z axis and the trunk 43 illustrated in FIG. 3 falls within a predetermined angle (for example, 20 degrees) is set as the reference trunk (the reference trunk 43S) (S4).

The trunk 43 is calculated in time series according to the frame rate of the camera 34, and the reference trunk 43S is a trunk 43 which satisfies the above condition that the time-series trunk 43 is within a predetermined angle, and is the latest captured one in the trunk capturing time calculated this time.

The trunk extraction unit 22 stores the capturing time of the frame of the reference trunk 43S. The trunk extraction unit 22 updates the capturing time of the frame if the trunk 43 calculated this time is the reference trunk 43S.

Figure 6:
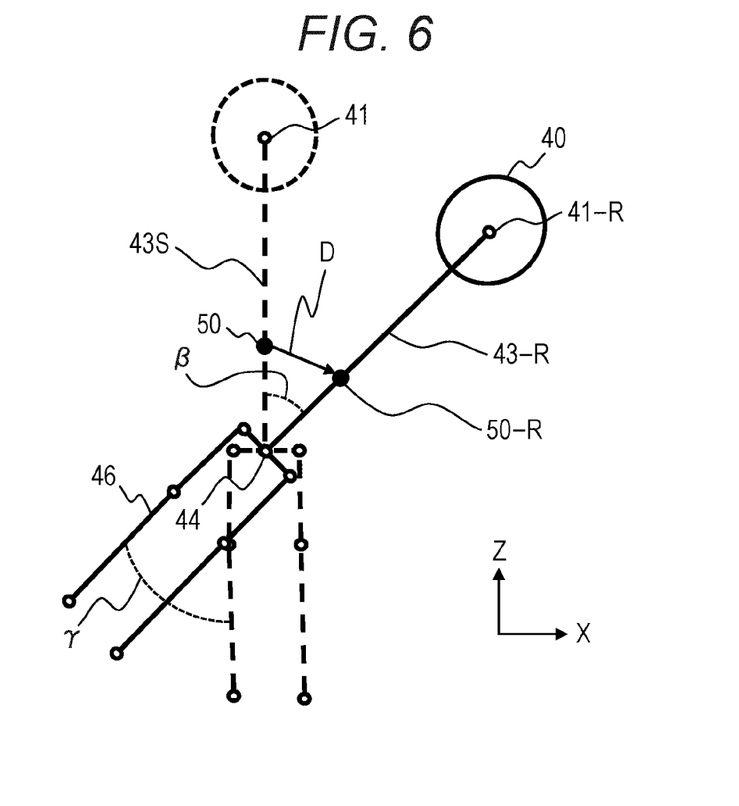
FIG. 6 is a diagram illustrating an example of a reference trunk of a sitting posture and an overturned trunk of the first embodiment of the invention.

The trunk extraction unit 22 calculates a deviation amount D from the trunk center 50 of the reference trunk 43S to the coordinates of the current trunk center 50 (S5). The deviation amount D can be represented by a difference (distance) between the coordinates of the trunk center 50 of the reference trunk 43S and the coordinates of the current trunk center 50-R as illustrated in FIG. 6. Further, a distance may be used as the deviation amount D, or the number of pixels between frames may be used in the case of two-dimensional expression.

FIG. 6 illustrates a state in which the subject 40 illustrated in FIG. 3 falls to the right side (the subject 40 is on the left side) in the drawing when observed from the position of the monitor 33 in FIG. 1. In FIG. 6, the trunk of the falling subject 40 is denoted by 43-R, the head center is denoted by 41-R, and the trunk center is denoted by 50-R.

The trunk extraction unit 22 calculates the moving direction (falling direction) of the trunk center 50 from the difference between the coordinates. The moving direction can be, for example, 0 degrees in front of the subject 40, the falling direction is 90 degrees when falling to the left side, and −90 degrees when falling to the right side. When the deviation amount D is 0 or near 0, the trunk extraction unit 22 sets a predetermined value (for example, a null value) indicating that there is no falling direction.

Next, in Step S6, the trunk extraction unit 22 calculates the acceleration $\alpha$ of the current trunk center 50 from the deviation amount D between the capturing time of the reference trunk 43S and the capturing time of the current trunk 43, the previous speed, and the previous capturing time of the trunk 43.

Next, the trunk extraction unit 22 calculates the angle $\beta$ (see FIG. 6) formed by a current trunk 43-R and the reference trunk 43S, and an angle $\gamma$ (see FIG. 6) formed by the leg 42 of the reference trunk 43S and the leg 42 of the current trunk 43 (S7).

In Step S8, it is determined whether the deviation amount D is equal to or larger than a predetermined threshold ThD. If the difference D is equal to or larger than the threshold ThD, the process proceeds to Step S12, and if less than the threshold ThD, the process proceeds to Step S9. The threshold ThD is set in advance to a value such that the deviation amount of the trunk center 50 indicates a sign of a fall.

In Step S9, it is determined whether the acceleration $\alpha$ is equal to or larger than a predetermined threshold Th$\alpha$. If the acceleration $\alpha$ is equal to or larger than the threshold Th$\alpha$, the process proceeds to Step S12. If the acceleration $\alpha$ is less than the threshold Th$\alpha$, the process proceeds to Step S10. The threshold Th$\alpha$ is set in advance to a value at which the acceleration of the trunk center 50 indicates a sign of a fall.

In Step S10, it is determined whether the angle $\beta$ of the trunk 43 is equal to or larger than a predetermined threshold Th$\beta$. If the angle $\beta$ is equal to or larger than the threshold Th$\beta$, the process proceeds to Step S12, and if smaller than the threshold Th$\beta$, the process proceeds to Step S10. The threshold Th$\beta$ is set in advance to a value at which the angle of the trunk 43 indicates a sign of a fall.

In Step S11, it is determined whether the angle $\gamma$ of the leg 42 is equal to or larger than a predetermined threshold Th$\gamma$. If the angle $\gamma$ is equal to or larger than the threshold Th$\gamma$, the process proceeds to Step S12. If the angle $\gamma$ is less than the threshold Th$\gamma$, the process proceeds to Step S1, and the process is repeated. The threshold Th$\gamma$ is set in advance to a value at which the angle of the leg 42 indicates a sign of a fall or the like.

Figure 7:
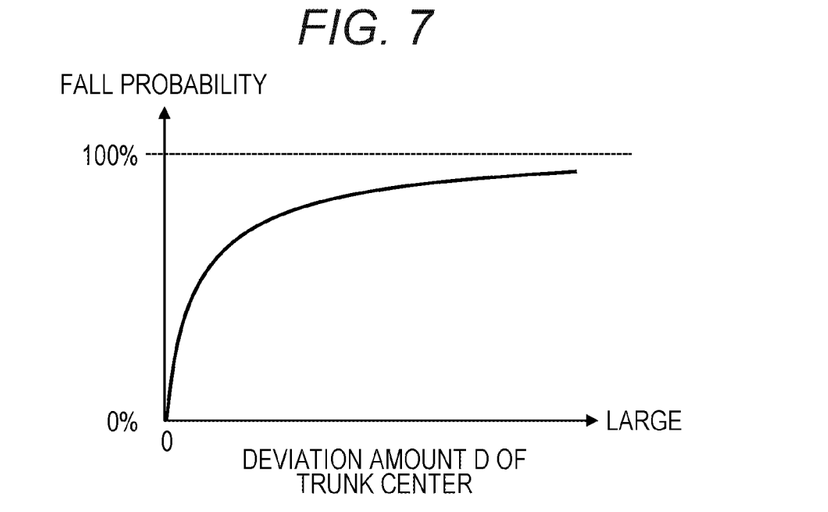
FIG. 7 is a graph illustrating an example of a deviation amount of a trunk center and a fall probability of the first embodiment of the invention.

In Step S12, the fall probability calculation unit 23 calculates the fall probability P based on the deviation amount D and the like. The fall probability P can be calculated from the deviation amount D of the trunk center 50 as illustrated in FIG. 7. In the example of FIG. 7, the fall probability P can be represented as follow.

Fall probability P=f1(D) Further, f1 is a predetermined function for calculating the fall probability P from the deviation amount D.

In this embodiment, the fall probability P is calculated from the acceleration $\alpha$ of the trunk center 50, the angle $\beta$ of the trunk 43, and the angle $\gamma$ of the leg 42 in addition to the deviation amount D. The fall probability P can be represented as follows.

Fall probability P=f2((D×w1)+($\alpha$×w2)+($\beta$×w3)+($\gamma$×w4)) Further, f2 is a predetermined function for calculating the fall probability P from the deviation amount D, the acceleration $\alpha$, and the angles $\beta$ and $\gamma$. Further, w1 indicates a weight coefficient of the deviation amount D, w2 indicates a weight coefficient of the acceleration $\alpha$, w3 indicates a weight coefficient of the angle $\beta$, and w4 indicates a weight coefficient of the angle $\gamma$.

Next, the fall probability calculation unit 23 acquires the falling direction calculated in Step S5 (S13), and determines whether there is a falling direction (S14). If the falling direction is other than the predetermined value (null value), the fall probability calculation unit 23 proceeds to Step S15 because the falling direction is determined, and otherwise proceeds to Step S19.

In Step S15, the warning generation unit 24 compares the fall probability P with a predetermined threshold ThP, and if the fall probability P is equal to or larger than the threshold ThP, it is determined that there is a sign of a fall, and the process proceeds to Step S16. If P is less than the threshold ThP, the process proceeds to Step S19.

In Step S16, since the warning generation unit 24 detects the sign of the fall of the subject 40, the warning generation unit 24 generates an image indicating the direction of correcting the posture (trunk) with respect to the subject 40 as a trunk correction image, and transmits the image to the monitor 33 of the living room 30.

Figure 8:
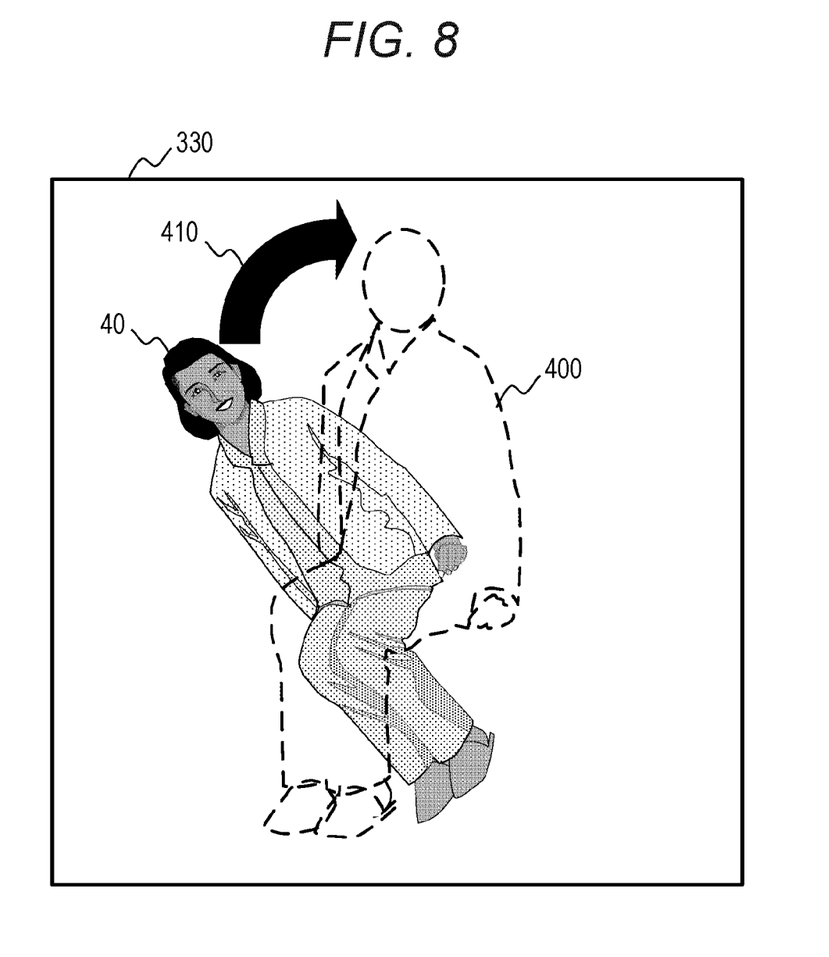
FIG. 8 is a diagram illustrating an example of a corrected image of a trunk of the first embodiment of the invention.

FIG. 8 is a diagram illustrating an example of a corrected image of the trunk. FIG. 8 illustrates a case where the subject 40 is likely to fall to the left side from the state of FIG. 3. On a screen 330 of the monitor 33 installed facing the subject 40, the current image of the subject 40 and the silhouette of the subject acquired from the frame that has generated the reference trunk 43S are displayed as a trunk correction image 400. Further, the direction in which the trunk is to be moved is displayed by an arrow 410 between the current image of the subject 40 and the trunk correction image 400.

The screen 330 of the monitor 33 is configured by a mirror image when observed from the subject 40. That is, when the subject 40 is likely to fall to the left side from the state of FIG. 3, the current image of the subject 40 is displayed on the screen 330 as being inclined to the left side. Then, the arrow 410 on the screen 330 is displayed so as to move the body to the right side when observed from the subject 40.

Next, in Step S17, the warning generation unit 24 turns over the light 35-L of the living room 30. The light 35-L is installed on the right side when viewed from the subject 40, and draws attention to the right side of the subject 40 who is currently likely to fall to the left side. The warning generation unit 24 turns on a light installed for a predetermined time in a direction opposite to the direction in which the subject 40 is likely to fall, thereby notifying that a fall can be avoided if the trunk is moved to the right side with respect to the subject 40. Further, the warning generation unit 24 may cause the light 35-L to blink until a predetermined time.

In this embodiment, an example is illustrated in which the lights 35 provided on both sides of the monitor 33 are turned on, but the invention is not limited to this. For example, speakers (not illustrated) may be provided on both sides of the monitor 33 or both ends of the long side of the bed 31, and sound may be output from the speakers on the opposite side to the falling direction. Further, instead of the warning by a warning device such as light or sound, the direction in which the trunk is moved by vibration may be instructed. In addition, a plurality of warning devices for notifying the subject 40 of a warning may be arranged around the subject 40, and a warning may be generated from the warning device in the direction opposite to the falling direction.

Next, the warning generation unit 24 outputs a warning indicating that a sign of a fall has occurred to the subject 40 in the living room 30 to the output device 14, and notifies a person in charge of the medical institution of a sign of a fall.

On the other hand, in Steps S14 and S15, in the case where there is no falling direction or the fall probability P is less than the threshold ThP in Step S19, the warning generation unit 24 outputs a message for adjusting the height or position of furniture or the bed 31 to the output device 14. Then, in Step S20, the warning generation unit 24 outputs a message prompting the user to install the cushion 32 to the output device 14. Then, the watching program 20 returns to Step S1 and repeats the above processing.

With the above processing, the watching system of this embodiment can extract a change in the trunk of the human body from a moving image of the human body, and detect a sign of a fall including the sitting posture with high accuracy.

In this embodiment, an example is described in which a sign of a fall is detected for a person (the subject 40) having a symptom whose posture is difficult to maintain, but in general, a sign of a fall may be detected for a human.

Further, in this embodiment, an example in which the skeleton is extracted from the moving image of the camera 34 and the fall probability P of the subject 40 is calculated has been described, but the invention is not limited to this. For example, a video processing server that obtains the moving image of the camera 34 and a skeleton extraction server that obtains the video from the video processing server and extracts the skeleton of the subject 40 (imaged person) may be operated independently. Then, the computer 10 of this embodiment may receive the time-series skeleton information from the skeleton extraction server and calculate the fall probability P of the captured person. Further, the time-series skeleton information may be any information that includes the time at which the image from which the skeleton information has been extracted is captured.

Second Embodiment

Figure 9:
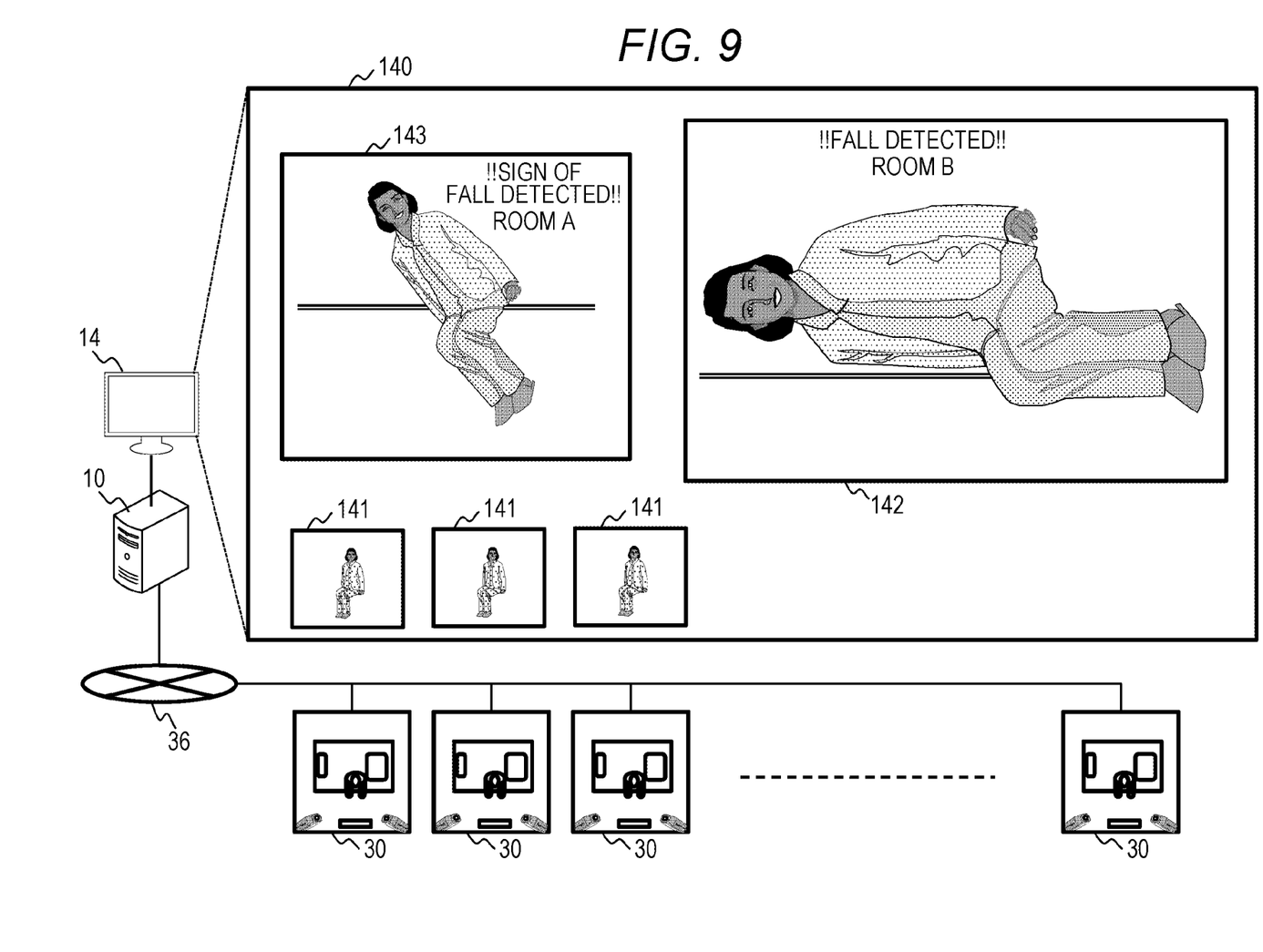
FIG. 9 is a diagram illustrating an example of a watching system of a second embodiment of the invention.

FIG. 9 is a diagram illustrating a second embodiment of the invention, and illustrating an example of a configuration of the watching system. The watching system according to this embodiment illustrates an example in which the subject 40 in a large number of living rooms 30 are monitored. The configuration in each living room is the same as in the first embodiment.

The computer 10 is connected to the cameras 34 and the like of a large number of the living rooms 30 via the network 36, acquires images (moving images) of the cameras 34 of the respective rooms 30, and calculates the fall probability P in the same manner as in the first embodiment.

The computer 10 displays the image of the camera 34 in each living room 30 on a screen 140 of the output device 14. In this embodiment, the computer 10 changes the size of the window of the living room 30 displayed in the screen 140 according to the magnitude of the fall probability P.

If the value of the fall probability P for each subject 40 in the living room 30 is less than a predetermined threshold ThP1, the computer 10 displays the image in the living room 30 with the smallest window 141 because there is no sign of a fall.

If the value of the fall probability P for each subject 40 in the living room 30 is equal to or larger than a predetermined threshold ThP2, the computer 10 determines that a fall has occurred, and displays the image in the living room 30 in the largest window 142. Further, the relationship between the thresholds is that Threshold ThP1<Threshold ThP2.

If the value of the fall probability P for each of the subjects 40 in the living room 30 is equal to or larger than the predetermined threshold ThP1 and less than the predetermined threshold ThP2, the computer 10 determines that a sign of a fall has occurred in the subject 40. Therefore, the image in the living room 30 is displayed in a window 143 of a medium size.

A warning message and a room name are displayed on the window 142 in which a fall has occurred and the window 143 in which a sign of a fall has occurred, so that the person in charge of the medical institution can be notified of the living room 30 in which an abnormality has occurred.

As described above, in the watching system of this embodiment, when the computer 10 monitors the subjects 40 of the large number of living rooms 30, a window is displayed for each living room 30 on the screen 140, and the image of the living room 30 where there is no sign of a fall is displayed in the window 141 of the smallest size, the image of the living room 30 where a sign of a fall has occurred is displayed in the window 143 of a medium size, and the image of the living room 30 where a fall has occurred is displayed in the window 142 of the largest size. In this embodiment, a person in charge of the medical institution that monitors the screen 140 can accurately grasp the living room 30 where an abnormality has occurred.

Third Embodiment

Figure 10:
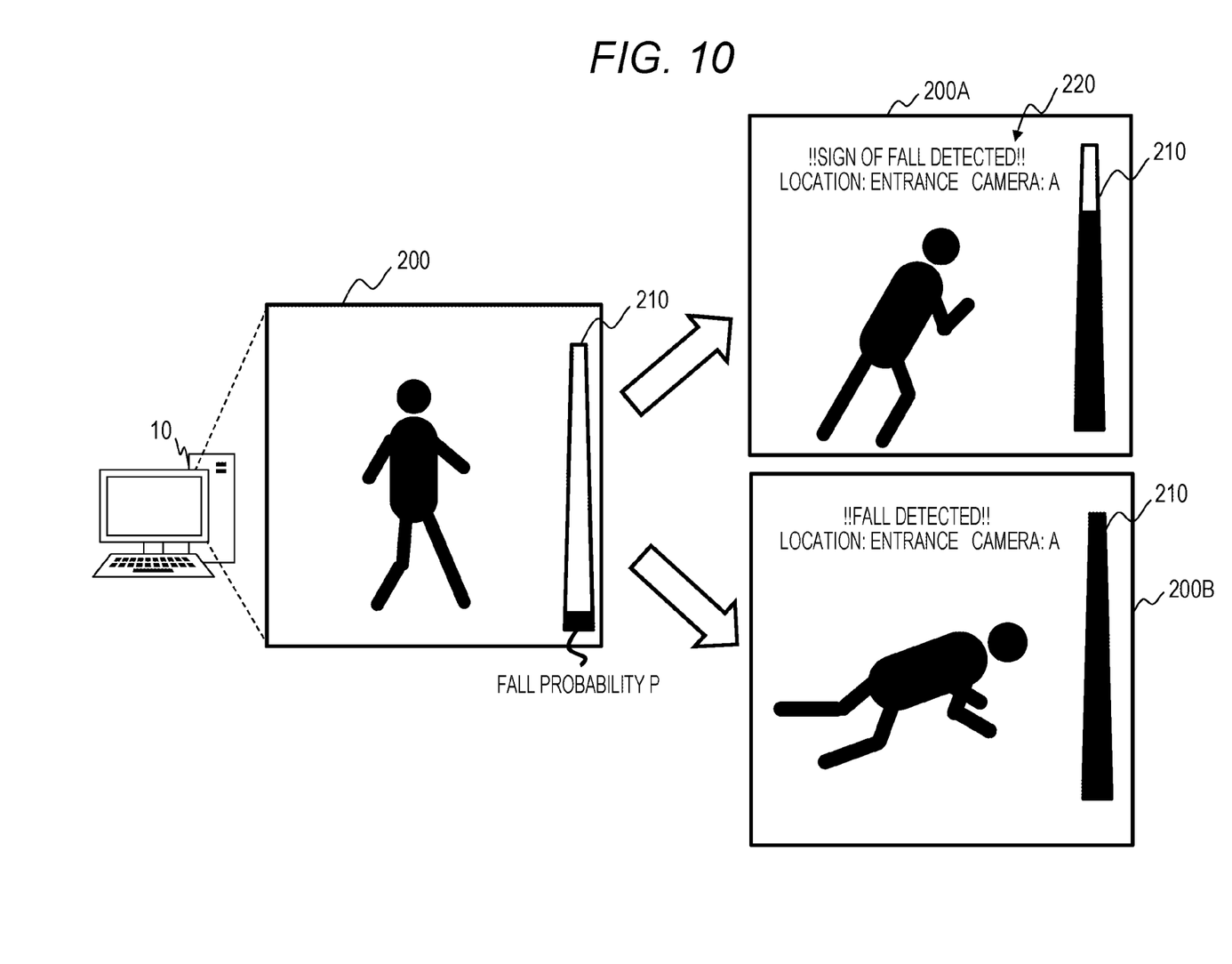
FIG. 10 is a diagram illustrating an example of the watching system that detects a sign of a fall during walking of a third embodiment of the invention.

FIG. 10 is a diagram illustrating a third embodiment of the invention, and illustrating an example in which a watching system monitors a pedestrian. In this embodiment, an example in which the camera 34 is installed in a passage or the like and a sign of a fall of a pedestrian passing through the passage is detected.

The watching system may be configured such that the monitor 33 and the light 35 of the first embodiment are deleted. In this embodiment, when monitoring an unspecified number of pedestrians, a fixed value set in advance is used as the position (ratio) of the trunk center 50.

FIG. 10 illustrates an example of a screen 200 of the output device 14 of the computer 10. The screen 200 displays an image of a pedestrian who does not have a sign of a fall, and a bar 210 indicating the fall probability P is displayed on the right side of the screen 200.

The bar 210 is configured such that the colored region extends upward in the drawing as the fall probability P increases. For example, as in a screen 200A, when the fall probability P indicates a sign of a fall (the threshold ThP1 or more), the colored region of the bar 210 extends upward, and in addition to the image of the pedestrian, a warning message and the position of the camera 34 are displayed.

Furthermore, when the fall probability P increases and becomes equal to or larger than the threshold ThP2, as in a screen 200B, the bar 210 becomes a colored region, and the computer 10 determines that a fall has occurred to the pedestrian, and in addition to the image of the pedestrian, a warning message and the position of the camera 34 are displayed.

As described above, the watching system according to this embodiment can detect a sign of a fall from a change in the trunk, so that the watching system is not limited to a person having a symptom whose posture is difficult to maintain, and in general, can monitor a person's walking and the like.

CONCLUSIONS

As described above, the watching systems of the first to third embodiments can be configured as follows.

(1) According to the invention, there is provided a watching system which calculates a fall probability (P) of an imaged person (the subject 40) to be fallen using a computer (10) which includes a processor (11) and a memory (12). The watching system includes a trunk extraction unit (22) that receives time-series skeleton information of the imaged person (40), calculates an angle between a head (the head center 41) and a waist (the waist center 44) of the imaged person (40) based on the skeleton information, extracts the angle as a trunk (43) of the imaged person (40), calculates a center of the trunk (43) as a trunk center (50) based on trunk information (110) set in advance, extracts a trunk (43) to be reference as a reference trunk (43S) from a time-series trunk (43) calculated from the time-series skeleton information, and holds a center of the reference trunk (43S), and a fall probability calculation unit (23) that calculates a distance between a trunk center (50) of the reference trunk (43S) and a trunk center (50) of the trunk (43) as a deviation amount (D), and calculates the fall probability (P) from the deviation amount (D).

With the above configuration, the computer 10 calculates the distance between the trunk center 50 of the reference trunk 43S and the trunk center 50 of the trunk 43 as the deviation amount D, and can calculate the fall probability P according to the value of the deviation amount D, and can detect a sign of a fall with high accuracy, including a sitting posture, based on a change in the trunk of a human body (imaged person).

(2) In the watching system according to (1), the trunk extraction unit (22) calculates a time-series trunk center (50) from the time-series trunk (43), and calculates an acceleration ($\alpha$) of the trunk center (50) from the time-series trunk center (50). The fall probability calculation unit (23) calculates the fall probability from the deviation amount (D) of the trunk center (50) and the acceleration ($\alpha$).

With the above configuration, by calculating the fall probability P from the acceleration $\alpha$ of the trunk center 50 in addition to the deviation D of the trunk center 50, a sign of a fall can be detected with high accuracy including the sitting posture, based on a change (the deviation amount D and the acceleration $\alpha$) of the trunk of a human body (imaged person).

(3) In the watching system according to (2), the trunk extraction unit (22) calculates an angle ($\beta$) of legs (42) from the time-series trunk (43). The fall probability calculation unit (23) calculates the fall probability (P) from the deviation amount (D) of the trunk center (50), the acceleration ($\alpha$), and the angle ($\gamma$) of the legs (42).

With the above configuration, by calculating the fall probability P from the acceleration $\alpha$ of the trunk center 50 and the angle of the leg 42 in addition to the deviation amount D of the trunk center 50, a sign of a fall can be detected with high accuracy including the sitting posture, based on a change (the deviation amount D, the acceleration $\alpha$, and the angle $\gamma$) of the trunk of a human body (imaged person).

(4) The watching system according to (1) further includes a warning generation unit (24) that determines a sign of a fall when the fall probability (P) is equal to or larger than a preset threshold (ThP, ThP1).

According to the above configuration, when a sign of a fall occurs in the imaged person, a person in charge of a medical institution using the computer 10 can be notified of an abnormality of the imaged person.

(5) In the watching system according to (4), the warning generation unit (24) outputs a predetermined warning (220) when the sign of the fall is determined.

With the above configuration, when a sign of a fall occurs in the imaged person, the computer 10 outputs a warning to notify a person in charge of a medical institution using the computer 10 or the imaged person of a sign of abnormality.

(6) In the watching system according to (4), the warning generation unit (24) outputs a trunk correction image (400) for correcting the trunk (43) of the imaged person (40) when the sign of the fall is determined.

With the above configuration, when a sign of a fall occurs in the imaged person, the computer 10 provides the trunk correction image 400 so as to provide a moving direction of the trunk to the imaged person.

(7) In the watching system according to (4), the trunk extraction unit (22) calculates a moving direction of the trunk center (50) from the time-series trunk center (50) as a falling direction. The warning generation unit (24) is connected to a plurality of warning devices (the lights 35) disposed around the imaged person (40), and generates a predetermined warning from the warning devices (35) in a direction opposite to the falling direction when the sign of the fall is determined.

With the above configuration, when a sign of a fall occurs in the imaged person, a warning is generated from the light 35 in a direction opposite to the falling direction among the lights 35 connected to the computer 10, so that the imaged person (the subject 40) can be urged to a direction to move the trunk.

Further, the invention is not limited to the embodiments described above, but includes various modifications. For example, the embodiments have been described in detail in order to help with understanding on the invention, but the invention is not limited to the one equipped with all the configurations. In addition, some of the configurations of a certain embodiment may be replaced with the one of the other embodiment. In addition, the configuration of the other embodiment may be added to the configuration of a certain embodiment. In addition, some of the configurations of each embodiment may be applied even when the other configurations are added, deleted, or replaced individually or in combination.

In addition, some or all of the configurations, the functions, the processing units, and processing devices may be realized in hardware by designing with an integrated circuit for example. In addition, the configurations and the functions may be realized in software by analyzing and executing a program which realizes the functions of a processor. Information such as a program, a table, and a file for achieving each function can be stored in a recording device such as a memory, a hard disk, or a solid-state drive (SSD), or a recording medium such as an integrated circuit (IC) card, a secure digital (SD) card, or a digital versatile disc (DVD).

In addition, only control lines and information lines considered to be necessary for explanation are illustrated, but not all the control lines and the information lines for a product are illustrated. In practice, almost all the configurations may be considered to be connected to each other.

What is claimed is:

1. A watching system for calculating a fall probability of an imaged person to be fallen using a computer which includes a processor and a memory operatively coupled to and in communication with the processor, comprising:
   the processor performs a trunk extraction that receives time-series skeleton information of the imaged person, calculates an angle between a head and a waist of the imaged person based on the skeleton information, extracts the angle as a trunk the imaged person, calculates a center of the trunk as a trunk center based on trunk information set in advance, extracts a trunk to be reference as a reference trunk from a time-series trunk calculated from the time-series skeleton information, and holds a center of the reference trunk;
   performs a fall probability calculation that calculates a distance between a trunk center of the reference trunk and a trunk center of the trunk as a deviation amount, and calculates the fall probability from the deviation amount based upon the deviation amount exceeding a predetermined deviation threshold; and
   generates a warning for a predetermined period of time in a direction opposite to the direction in which a subject is likely to fall.

2. The watching system according to claim 1, wherein the processor calculates a time-series trunk center from the time-series trunk, and calculates an acceleration of the trunk center from the time-series trunk center, and the processor calculates the fall probability from the deviation amount of the trunk center and the acceleration.

3. The watching system according to claim 2, wherein the processor calculates an angle of legs from the time-series trunk, and
   the processor calculates the fall probability from the deviation amount of the trunk center, the acceleration, and the angle of the legs.

4. The watching system according to claim 1, further comprising the processor determines a sign of a fall when the fall probability is equal to or larger than a preset threshold.

5. The watching system according to claim 4, wherein the processor outputs a predetermined warning when the sign of the fall is determined.

6. The watching system according to claim 4, wherein the processor outputs a trunk correction image for correcting the trunk of the imaged person when the sign of the fall is determined.

7. The watching system according to claim 4, wherein
   the processor calculates a moving direction of the trunk center from the time-series trunk center as a falling direction, and
   the processor is connected to a plurality of warning devices disposed around the imaged person, and generates a predetermined warning from the warning devices in a direction opposite to the falling direction when the sign of the fall is determined.

8. A watching method for calculating a fall probability of an imaged person to be fallen using a computer which includes a processor and a memory, comprising:
   the processor receiving time-series skeleton information of the imaged person, calculating an angle between a head and a waist of the imaged person based on the skeleton information, extracting the angle as a trunk of the imaged person, calculating the trunk center as a trunk center based on trunk information set in advance, extracting a trunk to be reference as a reference trunk from a time-series trunk calculated from the time-series skeleton information, and holds a center of the reference trunk;
   the processor calculating a distance between a trunk center of the reference trunk and a trunk center of the trunk as a deviation amount, and calculating the fall probability from the deviation amount based upon the deviation amount exceeding a predetermined deviation threshold; and
   the processor generating a warning for a predetermined period of time in a direction opposite to the direction in which a subject is likely to fall.

9. The watching method according to claim 8, wherein
   a time-series trunk center is calculated from the time-series trunk, and an acceleration of the trunk center is calculated from the time-series trunk center, and
   the fall probability is calculated from the deviation amount of the trunk center and the acceleration.

10. The watching method according to claim 9, wherein
    the angle of the legs is calculated from the time-series trunk, and
    the fall probability is calculated from the deviation amount of the trunk center, the acceleration, and the angle of the leg.

11. The watching method according to claim 8, further comprising determining, by the processor, a sign of a fall when the fall probability is equal to or larger than a preset threshold.

12. The watching method according to claim 11, wherein a predetermined warning is output when the sign of the fall is determined.

13. The watching method according to claim 11, wherein a trunk correction image for correcting the trunk of the imaged person is output when the sign of the fall is determined.

14. The watching method according to claim 11, wherein
- a moving direction of the trunk center is calculated from the time-series trunk center as a falling direction, and
- a predetermined warning is generated from a plurality of warning devices disposed around the imaged person in a direction opposite to the falling direction when the sign of the fall is determined.

15. A non-transitory computer-readable recording medium having stored therein a program for causing a computer which includes a processor and a memory to execute a process comprising:

receiving time-series skeleton information of the imaged person, calculating an angle between a head and a waist of the imaged person based on the skeleton information, extracting the angle as a trunk of the imaged person, calculating the trunk center as a trunk center based on trunk information set in advance, extracting a trunk to be reference as a reference trunk from a time-series trunk calculated from the time-series skeleton information, and holding a center of the reference trunk;

calculating a distance between a trunk center of the reference trunk and a trunk center of the trunk as a deviation amount, and calculating the fall probability from the deviation amount based upon the deviation amount exceeding a predetermined deviation threshold; and generating a warning for a predetermined period of time in a direction opposite to the direction in which a subject is likely to fall.

* * * * *